United States Patent [19]

Kompis et al.

[11] Patent Number: 4,774,249
[45] Date of Patent: Sep. 27, 1988

[54] PYRIMIDINE DERIVATIVES FOR TREATING MALARIA

[75] Inventors: Ivan Kompis, Oberwil; Rita Locher, Basel, both of Switzerland; Hans Maag, Upper Montclair, N.J.

[73] Assignee: Hoffmann-La Roche Inc., Nutley, N.J.

[21] Appl. No.: 112,908

[22] Filed: Oct. 23, 1987

Related U.S. Application Data

[60] Continuation of Ser. No. 837,447, Mar. 7, 1986, abandoned, which is a division of Ser. No. 598,119, Apr. 9, 1984, Pat. No. 4,590,270.

[30] Foreign Application Priority Data

Apr. 14, 1983 [CH] Switzerland .................... 2003/83
Feb. 10, 1984 [CH] Switzerland ...................... 633/84

[51] Int. Cl.⁴ ........................................ A61K 31/505
[52] U.S. Cl. ................................... 514/272; 514/275
[58] Field of Search ................................ 514/272, 275

[56] References Cited

U.S. PATENT DOCUMENTS 3,133,073  5/1964  Archer ............................... 546/124
4,053,475  10/1977  Lesher et al. ....................... 544/328
4,109,092  8/1978  Lesher et al. ....................... 544/328
4,438,267  3/1984  Daluge et al. ....................... 544/309

FOREIGN PATENT DOCUMENTS 122580   9/1984   European Pat. Off. ............ 544/328
2493848  11/1980  France ................................ 544/328
2609208  9/1976   Fed. Rep. of Germany ...... 544/328
3001328  7/1980   Fed. Rep. of Germany ...... 544/328
4911710  3/1974   Japan .................................. 544/328
762256   11/1956  United Kingdom ................. 544/328

OTHER PUBLICATIONS

PDR (1960) 15th Edition, p. 809.
Burger Medicinal Chemistry, Second Edition (1960), p. 42.
Kompis et al., Chem. Abstract 88-152540F.
Chem. Abstract 51-15607c.
Chem. Abstract 86-29868a.

Primary Examiner—Jerome D. Goldberg
Attorney, Agent, or Firm—Jon S. Saxe; Bernard S. Leon; Matthew Boxer

[57] ABSTRACT

The pyrimidine derivatives of formula I

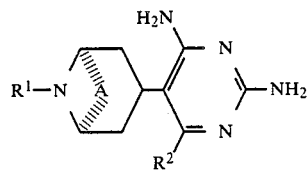

wherein $R^1$ is naphthyl, substituted naphthyl or substituted phenyl; $R^2$ is hydrogen or lower alkoxy; and A is an optionally present ethylene or 1,3-propylene, and wherein the diaminopyridine group has the exo-configuration when A is present, are described. These compounds are useful as antibacterial agents, antimalarial agents and antitumor agents, and can be used in combination with sulfonamides in the control of bacterial infections.

5 Claims, No Drawings

PYRIMIDINE DERIVATIVES FOR TREATING MALARIA

This is a continuation of application Ser. No. 837,447 filed Mar. 7, 1986, now abandoned, which is a divisional of Ser. No. 598,119 filed Apr. 9, 1984, now U.S. Pat. No. 4,590,270.

BRIEF SUMMARY OF THE INVENTION

The invention is related to compounds of the formula

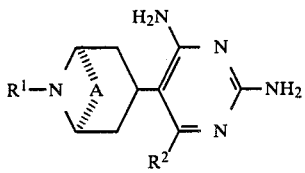

wherein $R^1$ is naphthyl, substituted naphthyl, or substituted phenyl; $R^2$ is hydrogen or lower alkoxy; and A is an optionally present ethylene or 1,3-propylene, and wherein the diaminopyrimidine group has the exo-configuration when A is present.

These compounds are useful as antibacterial agents, and antimalarial agents.

Pharmaceutical compositions containing the above compounds, processes for preparing the above compounds, and methods for treating bacterial infections, and malaria using the above compounds also form a part of the invention.

DETAILED DESCRIPTION OF THE INVENTION

The invention is concerned with pyrimidine derivatives of the formula

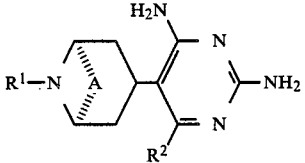

wherein $R^1$ is naphthyl, substituted naphthyl or substituted phenyl; $R^2$ is hydrogen or lower-alkoxy; and A is an optionally present ethylene or 1,3-propylene, and wherein the diaminopyrimidine group has the exo-configuration when A is present and salts thereof.

These compounds are useful as antibacterial agents, and antimalarial agents.

The invention is furthermore concerned with pharmaceutical compositions which contain a compound of formula I, a method for treating bacterial infections, or malaria which comprises administering a compound of formula I, and a process for the preparation of the compounds of formula I and intermediates products used in connection therewith.

More specifically, the invention relates to a pharmaceutical composition comprising an effective amount of a compound of the formula I or a salt thereof

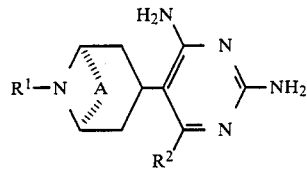

wherein $R^1$ is naphthyl, substituted naphthyl, or substituted phenyl; $R^2$ is hydrogen or lower-alkoxy; and A is optionally present ethylene or 1,3-propylene, and wherein the diaminopyrimidine group has the exo-configuration when A is present, and an inert carrier material.

The invention also relates to a method for treating bacterial infections which comprises administering to a host in need of such treatment an effective amount of a compound of the formula I or a salt thereof

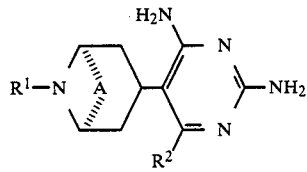

wherein $R^1$ is naphthyl, substituted naphthyl or substituted phenyl; $R^2$ is hydrogen or lower-alkoxy; and A is an optionally present ethylene or 1,3-propylene, and wherein the diaminopyrimidine group has the exo-configuration when A is present.

The invention also relates to a method for treating malaria which comprises administering to a host in need of such treatment an effective amount of a compound of the formula I or a salt thereof

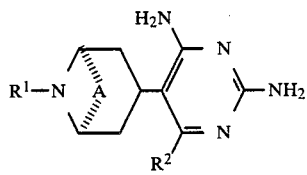

wherein $R^1$ is naphthyl, substituted naphthyl or substituted phenyl; $R^2$ is hydrogen or lower-alkoxy; and A is an optionally present ethylene or 1,3-propylene, and wherein the diaminopyrimidine group has the exo-configuration when A is present.

When $R^1$ is a substituted naphthyl or substituted phenyl, it is preferably singly or multiply substituted by lower-alkyl, lower alkylthio, lower alkoxy, halogen, amino, lower-alkyl-amino or di(lower-alkyl)-amino, nitro, trifluoromethyl, lower-alkoxycarbonyl, carboxyl, cyano or —CONHR$^3$ in which $R^3$ is hydrogen, lower-alkyl or the residue which is formed by removal of an amino group from an amino acid $R^3NH_2$. The naphthyl residue can be α-naphthyl or p-naphthyl. The term "lower" denotes substituents with 1–6 carbon atoms. Alkyl groups can be straight-chain or branched. Examples of such groups are methyl, ethyl, propyl, isopropyl and butyl. Preferred substituted phenyl substituents are 4-methoxyphenyl, 3,5-dimethoxyphenyl and 3,4,5-trimethoxyphenyl. Examples of amino acids $R^3NH_2$ are glycine, β-alanine, aspartic acid and glutamic acid. A preferred group of compounds of formula I are those in which $R^1$ is substituted phenyl. Furthermore, there are preferably compounds of formula I in which A is ethylene. These compounds can be represented by the formula

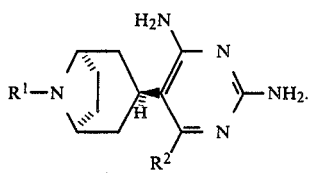  IA

In another respect the invention is concerned with compounds of the formula

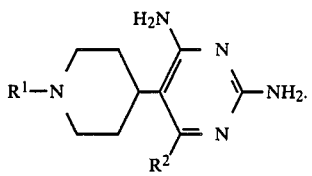  IB

The compounds of formula I can be prepared in accordance with the invention by
(a) treating a compound of the formula

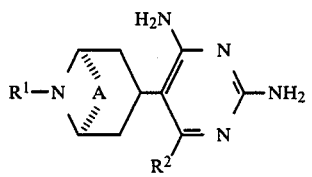  II wherein X is chlorine or bromine and $R^1$ and A are as described above, with a reducing agent, or
(b) reacting a compound of the formula

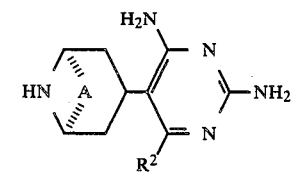  III with a compound of the formula $R^{11}$-Z, in which $R^{11}$ is naphthyl or substituted naphthyl or substituted phenyl, the substituents of which are inert under the reaction conditions, and Z is halogen or nitro, or
(c) reacting a compound of formula II with an alkali metal lower-alkylate, and, if desired, modifying a substituent contained in $R^1$ in the reaction product.

Suitable reducing agents for the removal of the chlorine or bromine substituent X from a compound of formula II are hydrogen in the presence of noble metal catalysts, such as Pd/carbon; or nascent hydrogen, e.g. Zn/glacial acetic acid, or amalgamated zinc in NaOH. The reduction can be undertaken in a manner known per se. The catalytic hydrogenation is conveniently carried out at room temperature in an inert solvent, e.g. aqueous acetic acid, or ethanol. The reduction with nascent hydrogen is conveniently carried out while heating, e.g. at temperatures up to the reflux temperature of the reaction mixture.

The N-substitution of a compound of formula III can be effected in a manner known per se. There are conveniently employed in this process variant compounds of formula $R^{11}$-Z in which there are contained substituents which are inert under the reaction conditions and which activate the substituent Z for the reaction with the compound III. The reaction is conveniently carried out in an inert solvent, such as acetonitrile or dimethyl sulfoxide in the presence of an acid-binding agent, such as alkali or alkaline earth hydroxides or carbonates while heating, e.g. up to the reflux temperature of the reaction mixture. There are preferably employed in this process variant compounds of formula $R^{11}$-Z in which $R^{11}$ is substituted by lower-alkoxy, halogen, nitro, trifluoromethyl, cyano or lower-alkoxycarbonyl. Z is preferably halogen, especially fluorine.

The reaction of a compound of formula II with an alkali metal lower alkylate can be undertaken by heating a compound of formula II with an alkali metal lower alkylate in the alcohol corresponding to the alkylate, e.g. to temperatures up to the reflux temperature. Examples of alkali metal lower alkylates are sodium and potassium methylate or ethylate.

Substituents contained in $R^1$ in the thus-obtained compounds of formula I can be modified. For example, an alkoxycarbonyl group can be saponified to the carboxy group or can be transformed into a carbamoyl group; a carboxy group can be amidated to a group $CONHR^3$; a nitro group can be reduced to the amino group, whereupon the amino group can be alkylated or diazotized and replaced with a halogen atom. These reactions can be carried out according to methods and under conditions which are generally known for the saponification of ester groups, amidation of carboxylic acid or carboxylic acid ester groups, reduction of nitro groups to amino groups alkylation of the latter as well as replacement of aromatic amino groups with other groups (Sandmeyer reaction). Compounds of formula I in which $R^1$ is carboxyl or —$CONHR^3$ are conveniently manufactured by saponifying an obtained compound of formula I in which $R^1$ is lower-alkoxycarbonyl and optionally reacting the thus-obtained carboxylic acid with a lower-alkylamine or an amino acid $R^3NH_2$ in the presence of condensation agents, such as dicyclohexylcarbodiimide or carbonyldiimidazole.

The compounds of formula I can be converted into acid addition salts, especially those which are customary in pharmaceutical preparations, by treatment with inorganic acids (e.g. hydrochloric acid, sulphuric acid, phosphoric acid etc) or organic acids (e.g. formic acid, acetic acid, succinic acid, lactic acid, citric acid, maleic acid, fumaric acid, tartaric acid, methanesulphonic acid, p-toluenesulphonic acid etc).

The compounds of formula II also form a part of the invention. They can be prepared as indicated in the following Formula Scheme and as described in detail in the Examples.

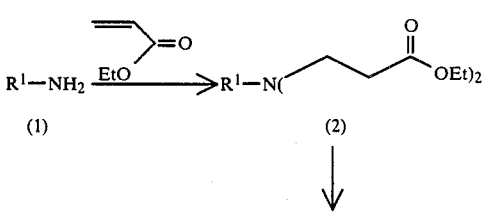

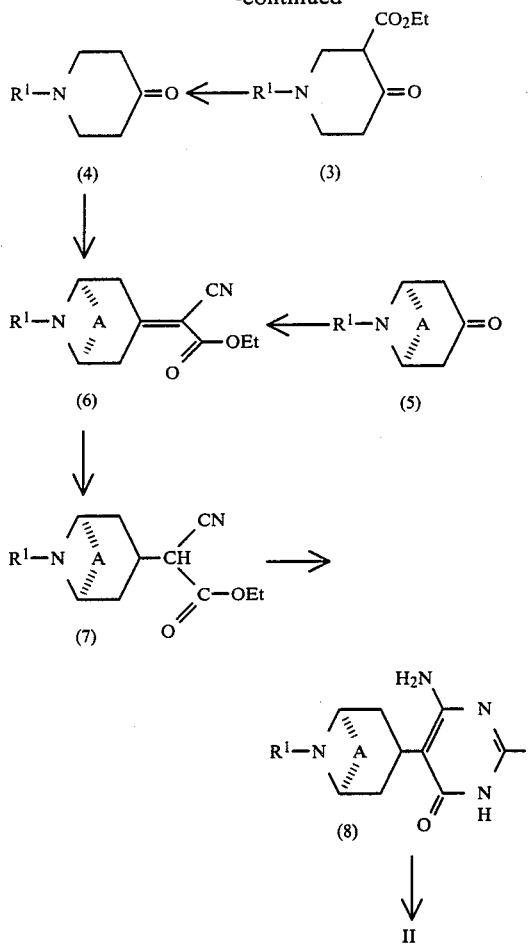

By reacting a correspondingly substituted aniline or a naphthylamine (1) with acrylic acid ethyl ester there is obtained the tertiary amine (2) and therefrom by Dieckmann condensation hydrolysis and decarboxylation of the β-ketoester (3) the piperidone (4). The Knoevenagel condensation with the cyanoacetic acid ethyl ester of (4) or (5) (Tetrahedron 28, 155–165 [1972]) and Bull. Chem. Soc. Japan 44, 1708–9 [1971]) yields (6) which is converted into (7) by reduction of the conjugated double bond. The reduction of compounds (6) in which X is present is conveniently carried out with LiAlH$_4$, in which case (7) is obtained as an isomer mixture in which the cyanoacetic acid residue has the endo- or exo-configuration. The exo-isomer which is required for the preparation of the preferred compounds IA can be separated in a manner known per se, e.g. by chromatography. Condensation of (7) with guanidine yields the pyrimidone (8) from which II can be obtained by halogenation. The reaction (7)→(8)→II can be carried out by analogy with known procedures which are described e.g. in German Offenlegungsschrift 2 003 578.

The compounds of formula I are pharmacologically active. In particular, they are active antibacterially and against malaria pathogens.

The compounds of formula I are useful as antibacterial agents and, are useful as antimalarial agents.

The compounds of formula I inhibit dihydrofolate reductase and potentiate the antibacterial activity of sulfonamides. They can also be used in combination with antibacterially-active sulfonamides as agents for the control of bacterial infections.

It has been found that exo-2,4-diamino-5-[8-(3,5-dimethoxyphenyl)-8-azabicyclo[3.2.1]oct-3-yl]pyrimidine (A) is active in an inhibitory concentration IC$_{50}$ of 3.3 mmol in the case of dihydrofolate reductase from E. coli. In the case of in vitro experiments an minimum inhibitory concentration of 0.1–1.6 μg/ml has been determined for compound A against Bacteroides fragilis strains. Against the malaria pathogen P. falciparum compound A in vitro showed an ID$_{50}$ of 1.4 μg/l (strain T9) and 0.9 μg/l (strain 13). In comparison to this, values of 79 and 45 μg/l, respectively, were determined for the known pyrimethamine.

Examples of sulfonamides which are potentiated by the compounds of formula I are those of the pyrimidine, isoxazole, oxazole and pyrazine series such as sulfadiazine, sulfadimethoxine, sulfadoxine, sulfamerazine, sulfameter, sulfamethazine, 6-methoxy-4-sulfanilamidopyrimidine, sulfamethoxazole, sulfisoxazole, 3-sulfanilamido-4,5-dimethyl-isoxazole, sulfamoxole and sulfalen.

The compounds of formula I can be used as pharmaceutical preparations in admixture with an organic or inorganic inert carrier material suitable for oral, rectal or parenteral application, e.g. water, gelatine, gum arabic, lactose, starch, magnesium stearate, talc, vegetable oils, polyalkylene glycols, Vaseline, etc. The pharmaceutical preparations can be present in solid form, e.g. as tablets, dragées, suppositories, capsules; in semi-solid form, e.g. as salves; or in liquid form, e.g. as solutions, suspensions or emulsions. If desired, they are sterilized and/or contain further adjuvants, such as preserving, stabilizing, wetting or emulsifying agents, agents for the improvement of flavour, salts for varying the osmotic pressure or buffer substances. The preparation of the pharmaceutical compositions can be effected in the manner which is familiar to the person skilled in the art.

In the prophylaxis of malaria, the compounds of formula I, e.g. compound A can be used in dosages of from 25 mg to 50 mg for an adult. Preferably, the compounds of formula I are used in combination with a long-acting sulfonamide such as sulfadoxine. Suitably, a combination of 1 part by weight of compound A and 10 to 20 parts by weight of sulfadoxine are used. In the prophylaxis of malaria, a dosage of 500 mg once per week of such a combination can be used for an adult. In the treatment of malaria, a single dosage of 1000–1500 mg of the above combination can be used for an adult.

The following Examples further illustrate the invention.

EXAMPLE 1

180 mg of exo-4-chloro-2,6-diamino-5-[8-(4-methoxyphenyl)-8-azabicyclo[3.2.1]oct-3-yl]pyrimidine were dissolved in 20 ml of a mixture of acetic acid and water (1:1) and hydrogenated in the presence of 100 mg of 10% palladium/carbon catalyst until hydrogen was no longer taken up or the reaction was complete in accordance with thin-layer chromatography. The catalyst was removed by filtration over a filter aid and the filtrate was evaporated to dryness. The residue was suspended in water and the suspension was adjusted to pH 9 by addition of aqueous ammonium hydroxide. Filtration yielded a product which was chromatographed on silica gel with chloroform/methanol (9:1). Subsequent crystallization from methanol yielded exo-2,4-diamino- 5-[8-(4-methoxyphenyl)-8-azabicyclo[3.2.1]oct-3-yl]pyrimidine of melting point 242°.

The starting material was prepared as follows:

A. 3.0 g of 8-(4-methoxyphenyl)-8-azabicyclo[3.2.1]octan-3-one were dissolved in 6 ml of dimethylformamide and treated with 1.8 ml of cyanoacetic acid ethyl ester, 0.2 ml of piperidine and 58 mg of β-alanine. The mixture was heated to 50° for 28 hours while stirring. After cooling to room temperature, the mixture was diluted with ether, washed four times with water, dried over sodium sulfate and concentrated under reduced pressure. Chromatography of the residue on 250 g of silica gel with hexane/ethyl acetate (3:2) yielded ethyl cyano-[8-(4-methoxyphenyl)-8-azabicyclo[3.2.1]octanylidene]acetate as a white solid, melting point 121°-122° (from isopropyl ether).

B. 1.82 g of the thus-obtained compound were dissolved in 22 ml of tetrahydrofuran under argon. The mixture was cooled to −10°, treated with 110 mg of lithium aluminum hydride, stirred at −10° C. for 10 minutes and thereafter treated with saturated aqueous ammonium chloride solution and water. The thick suspension was filtered through filter paper and the residue was washed thoroughly with ethyl acetate. The organic phase of the filtrate was washed twice with water, dried over sodium sulfate and concentrated. The residue was chromatographed on 200 g of silica gel (230–400 mesh) with hexane/ethyl acetate (3:1). There were obtained 630 mg of ethyl rac-(exo)-α-cyano-[8-(4-methoxyphenyl)-8-azabicyclo[3.2.1 octane]octane]-3-acetate as an oil besides the endo-isomer.

C. An ethanolic sodium ethoxide solution was freshly prepared by dissolving 10 mmol of sodium in 12 ml of absolute ethanol under argon. The solution was treated with 10 mmol of guanidine hydrochloride and stirred at room temperature for 20 minutes. Thereafter, 5 mmol of the previously obtained α-cyanoacetate (exo-isomer) were added. The mixture was heated to reflux for 4 hours, cooled to room temperature and left in the refrigerator overnight. The solid was filtered off, washed well with water and dried. There was obtained exo-2,6-diamino-5-[8-(4-methoxyphenyl)-8-azabicyclo[3.2.1]oct-3-yl]-4(3H)-pyrimidinone, melting point above 260° C. (from methanol/chloroform).

D. 10 mmol of the previously obtained pyrimidinone were suspended in 15 ml of POCl3 and treated with 2.6 ml of N,N-dimethylaniline. The mixture was heated to reflux (105° C.) for 1.5 hours, and cooled to room temperature. About ⅔ of the phosphorus oxychloride were removed under reduced pressure. The viscous residue was added cautiously to ice and the aqueous suspension obtained was left to stand at room temperature for 5 days. The pH of the reaction mixture was adjusted to about 10 by by addition of 25% aqueous ammonium hydroxide solution, the product was filtered off and washed with water and subsequently with ethanol. Thereafter, the product was chromatographed on silica gel with chloroform/methanol (9:1). From 310 mg of exo-2,6-diamino-5-[8-(4-methoxyphenyl)-azabicyclo[3.2.1]oct-3-yl]-4-(3H)-pyrimidinone there were obtained 180 mg of exo-4-chloro-2,6-diamino-5-[8-(4-methoxyphenyl)-8-azabicyclo[3.2.1]oct-3-yl]pyrimidine.

EXAMPLE 2

In analogy to Example 1, from 1.6 g of exo-4-chloro-2,6-diamino-5-[8-(3,5-dimethoxyphenyl)-8-azabicyclo[3.2.1]-oct-3-yl]pyrimidine there were obtained 980 mg of exo-2,4-diamino-5-[8-(3,5-dimethoxyphenyl)-8-azabicyclo[3.2.1]oct-3-yl]pyrimidine, melting point 261°-262° C. (from methanol).

The starting material was prepared in analogy to the process described in Example 1, paragraphs A-D, starting from 8-(3,5-dimethoxyphenyl)-8-azabicyclo[3.2.1]octan-3-one via ethyl cyano-[8-(3,5-dimethoxyphenyl)-8-azabicyclo[3.2.1]octanylidene]acetate, melting point 116° C. (from isopropyl ether), ethyl rac-(exo)-α-cyano-[8-(3,5-dimethoxyphenyl)-8-azabicyclo[3.2.1]octane-3]acetate, mp. 92°-93° C. (from ethanol) and exo-2,6-diamino-5-[8-(3,5-dimethoxyphenyl)-8-azabicyclo[3.2.1]oct-3-yl]-4-(3H)-pyrimidinone, melting point 193°194° C. (from ethanol/water).

The ethyl cyano-[8-(3,5-dimethoxyphenyl)-8-azabicyclo[3.2.1]octanylidene]acetate can be reduced as follows:

0.7 g of lithium were dissolved in 150 ml of dry, distilled ammonia at −78° C. and treated dropwise under nitrogen during 20 minutes with a solution of 8.9 g of ethyl cyano-[8-(3,5-dimethoxyphenyl)-8-azabicyclo[3.2.1]octanylidene]acetate and 2.35 g of phenol in 50 ml of dry tetrahydrofuran. The mixture was left to stir for 30 minutes, whereupon 5 g of ammonium chloride were added. The ammonia was distilled off, the residue was taken up in ethyl acetate, filtered and the filtrate was evaporated. Chromatography of the crude product on silica gel with hexane/ethyl acetate (4:1) gave, besides a small amount of endo-isomer, 7.8 g of ethyl rac-(exo)-α-cyano-[8-(3,5-dimethoxyphenyl)-8-azabicyclo[3.2.1]octane-3]acetate of melting point 92°-93° C. (from ethanol).

EXAMPLE 3

21.5 g of 2,4-diamino-6-chloro-5-[1-(4-methoxyphenyl)-4-piperidinyl]pyrimidine were dissolved in 350 ml of a mixture of acetic acid and water (1:1) and hydrogenated in the presence of 7 g of 10% palladium/carbon catalyst until the hydrogen uptake ceased or the reaction was complete in accordance with thin-layer chromatography. The catalyst was filtered off over a filter aid and the filtrate was evaporated to dryness. The residue was suspended in water and the pH was adjusted to 9 by addition of aqueous ammonium hydroxide. Filtration yielded a crude product which was chromatographed on silica gel with chloroform/methanol (19:1). There were obtained 8.7 g of 2,4-diamino-5-[1-(4-methoxyphenyl)-4-piperidinyl]pyrimidine of melting point 224°-225° C.

The starting material was prepared as follows:

A. 32.3 g of diethyl 3,3'-[(4-methoxyphenyl)-imino]dipropionate in 40 ml of xylene were added under argon to a freshly prepared solution of sodium ethoxide in absolute ethanol (2.3 g of sodium in 55 ml of ethanol). The mixture was heated slowly to about 110° C., by which means the ethanol was distilled off. Thereafter, the mixture was heated for a further 2 hours. The mixture was cooled to room temperature and poured on to ice. After neutralization with concentrated hydrochloric acid, the mixture was extracted with ether. The extract was washed three times with water, dried over sodium sulfate and evaporated. The product was chromatographed on silica gel with hexane/ethyl acetate (9:1) and yielded ethyl 1-(p-methoxyphenyl)-4-oxo-3-piperidinecarboxylate as a yellow oil.

B. 57.9 g of the thus-obtained carboxylate were heated to reflux for 1 hour in 225 ml of 6N hydrochloric acid. After cooling to about 2° C., the mixture was neutralized by addition of 110 ml of 50% aqueous sodium hydroxide and extracted with ether. The organic phase was washed three times with water, dried over sodium sulfate and concentrated. The residue was recrystallized from ethanol. There was obtained 1-(p-methoxyphenyl)-4-piperidone, melting point 69° C. (from ethanol).

C. 20.5 g of 1-(p-methoxyphenyl)-4-piperidone were dissolved in 200 ml of benzene and treated with 1.2 g of acetic acid, 0.85 ml of piperidine and 14.5 g of cyanoacetic acid ethyl ester. The mixture was heated to reflux for 3 hours, the reaction water being removed by means of a Dean-Stark trap. After cooling to room temperature, the mixture was diluted with ether and washed three times with 2N sodium bicarbonate solution and once with water. The organic extract was dried over sodium sulfate and concentrated. The oily residue was triturated with ethanol and left in the refrigerator overnight. The solid was filtered off and washed with ethanol and isopropyl ether, there being obtained 24.1 g of product. Recrystallization from ethanol yielded ethyl cyano-[1-(p-methoxyphenyl)-4-piperidinylidene]acetate, melting point 87° C.

D. 22.5 g of the thus-obtained compound were dissolved in 500 ml of ethanol and 200 ml of methanol and hydrogenated up to the end of the hydrogen uptake with 5 g of 10% palladium-carbon catalyst (50% in water) while stirring vigorously at room temperature. After filtration over a filter aid, the filtrate was evaporated under reduced pressure and the residue was crystallized from a small amount of isopropyl ether. There was obtained ethyl α-cyano-[1-(4-methoxyphenyl)-4-piperidine]acetate, melting point 65° C.

E. The thus-obtained compound was condensed with guanidine in accordance with Example 1, paragraph (C). There was obtained 2,6-diamino-5-[1-(4-methoxyphenyl)-4-piperidinyl]-4-(3H)-pyrimidinone, melting point 308° C. (from dimethylformamide/water).

F. In analogy to Example 3, paragraph (C), from the thus-obtained pyrimidinone there was obtained 2,4-diamino-6-chloro-5-[1-(4-methoxyphenyl)-4-piperidinyl]pyrimidine, melting point 254° C. (decomposition, from ethanol).

EXAMPLE 4

In analogy to Example 3, from 5.7 g of 2,4-diamino-6-chloro-5-[1-(3,5-dimethoxyphenyl)-4-piperidinyl]-pyrimidine there were obtained 4.8 g of crude 2,4-diamino-5-[1-(3,5-dimethoxyphenyl)-4-piperidinyl]-pyrimidine, from which there were obtained 3.2 g of pure product of melting point 217° C. after chromatography and recrystallization from methanol.

The starting material was prepared as follows:

A. A mixture of 50.4 g of 3,5-dimethoxyaniline, 6.0 g of copper (I) chloride, 46.0 g of acetic acid and 100 g of ethyl acrylate was heated to reflux for 19 hours while stirring. After cooling to room temperature, the mixture was diluted with about 30 ml of methylene chloride and washed successively three times with 300 ml of water, three times with 300 ml of 10% aqueous ammonium hydroxide and again three times with 300 ml of water. The organic phase was dried over sodium sulfate and evaporated under reduced pressure. The residue was chromatographed on 1.5 kg of silica gel (230–400 mesh) with hexane/ethyl acetate (4:1) under medium pressure. There were obtained 70.9 g of diethyl 3,3'-(3,5-dimethoxyphenyl)-imino]dipropionate as a yellow oil, b.p. 139° C./0.09 mm.

B. From diethyl 3,3'-[(3,5-dimethoxyphenyl)-imino]-dipropionate there were obtained in analogy to Example 3, paragraph (A), ethyl 1-(3,5-dimethoxyphenyl)-4-oxo-3-piperidinecarboxylate, melting point 60°–61° C.

C. 12.52 g of the previously mentioned carboxylate were heated on the steam-bath in 81.6 ml of 1N sodium hydroxide solution while stirring vigorously for 2 hours. After cooling to room temperature, the mixture was extracted with ether, the extract was washed twice with water, dried over sodium sulfate and evaporated. The residue was chromatographed on silica gel with hexane/ethyl acetate (4:1) and yielded 4.8 g of 1-(3,5-dimethoxyphenyl)-4-piperidone as a yellow oil.

D. In analogy to Example 3, paragraph (C), from the previously obtained piperidone there were obtained ethyl cyano-[1-(3,5-dimethoxyphenyl)-4-piperidinylidene]acetate, melting point 115° C. (from methanol).

E. 19.2 g of the previously mentioned compound were dissolved in 400 ml of ethyl acetate and hydrogenated with 6 g of 10% palladium/carbon catalyst (50% in water). 19.7 g of ethyl α-cyano-1-(3,5-dimethoxyphenyl)-4-piperidine]acetate were obtained as an oil.

F. Ethyl α-cyano-[1-(3,5-dimethoxyphenyl)-4-piperidine]acetate was condensed with guanidine in analogy to Example 1, paragraph (C). There was obtained 2,6-diamino-5-[1-(3,5-dimethoxyphenyl)-4-piperidinyl]-4-(3H)-pyrimidinone, melting point above 250° C. (from dimethylformamide/water).

G. 2,6-Diamino-5-[1-(3,5-dimethoxyphenyl)-4-piperidinyl]-4-(3H)-pyrimidinone was converted in analogy to Example 3, paragraph (D), into 2,4-diamino-6-chloro-5-[1-(3,5-dimethoxyphenyl)-4-piperidinyl]-pyrimidine, melting point 241°–242° C. (from methanol/chloroform).

EXAMPLE 5

In analogy to Example 1, from 0.4 g of exo-4-chloro-2,6-diamino-5-[8-(3,4,5-trimethoxyphenyl)-8-azabicyclo[3.2.1]oct-3-yl]pyrimidine there were obtained 250 mg of exo-2,4-diamino-5-[8-(3,4,5-trimethoxyphenyl)-8-azabicyclo[3.2.1]-oct-3-yl]pyrimidine, m.p. 247°–248° C. (from methanol).

The starting material was prepared in analogy to the process described in Example 1, paragraph A-D, starting from 8-(3,4,5-trimethoxyphenyl)-8-azabicyclo[3.2.1]octan-3-one, m.p. 144°–145° C. (from methanol), via
ethyl cyano-[8-(3,4,5-trimethoxyphenyl)-8-azabicyclo[3.2.1]octanylidene]acetate, m.p. 107°–108° C.,
ethyl rac-(exo)-α-cyano-[8-(3,4,5-trimethoxyphenyl)-8-azabicyclo[3.2.1]octane-3]acetate (yellowish oil) and
exo-2,6-diamino-5-[8-(3,4,5-trimethoxyphenyl)-8-azabicyclo[3.2.1]oct-3-yl]-4-[3H]-pyrimidinone, m.p. 265° C. (dec.) from methanol-water).

EXAMPLE 6

In analogy to Example 3, from 5.6 g of 2,4-diamino-6-chloro-5-[1-(3,4,5-trimethoxyphenyl)-4-piperidinyl]-pyrimidine there were obtained 1.0 g of 2,4-diamino-5-[1-(3,4,5-trimethoxyphenyl)-4-piperidinyl]pyrimidine, m.p. 239°–240° C. (from methanol).

The starting material was prepared in analogy to the process described in Example 3, paragraphs C-F, from 1-(3,4,5-trimethoxyphenyl)-4-piperidine via ethyl 2-cyano-2-[1-(3,4,5-trimethoxyphenyl)-4-piperidinylidene]acetate, m.p. 111° C., yellow crystals from isopropanol, ethyl 2-cyano-2-[1-(3,4,5-trimethoxyphenyl)-4-piperidinyl]acetate, colourless oil, and 2,6-diamino-5-[1-(3,4,5-trimethoxyphenyl)-4-piperidinyl]-4-3(H)-pyrimidinone, m.p. >250° C. (dec.) (from ethanol).

EXAMPLE 7

A mixture of 1 g of 2,4-diamino-5-(4-piperidyl)-pyrimidine, 0.71 g of 4-fluoronitrobenzene and 0.7 g of potassium carbonate in 20 ml of acetonitrile were boiled at reflux for 72 hours with the exclusion of moisture. After cooling to room temperature, the mixture was filtered, the residue was washed with water, methanol and ether and recrystallized from dimethyl sulfoxide. This gave 1.36 g of 2,4-diamino-5-[1-(p-nitrophenyl)-4-piperidinyl]-pyrimidine. Melting point above 250° C.

Preparation of the starting material:

A solution of 26 g of 2,4-diamino-5-(1-benzyl-4-piperidinyl)pyrimidine in 700 ml of ethanol and 20 ml of acetic acid was hydrogenated over 5 g of Pd/C 10% at room temperature and normal pressure up to the standstill of the hydrogen uptake, whereupon it was filtered off from catalyst. The filtrate was concentrated and the crystalline residue was dissolved in 100 ml of water. Chromatography on Dowex 1 (×10 200–400 mesh) (a cation exchange resin) gave 2,4-diamino-5-(4-piperidyl)-pyrimidine of melting point 230°–231° C. (dec.) (from water).

EXAMPLE 8

1 g of 2,4-diamino-5-[1-(p-nitrophenyl)-4-piperidinyl]pyrimidine was dissolved in 50 ml of water and 10 ml of conc. hydrochloric acid, treated with 700 mg of iron powder and stirred at 80° C. for 45 minutes. The mixture was filtered over a filter aid, the filtrate was cooled to 0°–5° C., diazotized with 210 mg of sodium nitrite in 2 ml of water and the resulting diazonium solution was added dropwise at 0°–5° C. to a solution of copper (I) chloride (prepared from 250 mg of copper (II) sulfate pentahydrate, 80 mg of sodium chloride and 70 mg of sodium bisulfite) in 0.8 ml of hydrochloric acid. Thereafter, the reaction mixture was heated at 90° C. for 1 hour, treated with active carbon, filtered and concentrated to 50 ml. The residue was neutralized with ammonium hydroxide, filtered off and the product obtained after distilling off the water was chromatographed on silica gel with CHCl3/EtOH (9:1). Recrystallization from ethanol yielded 2,4-diamino-5-[1-(p-chlorophenyl)-4-piperidinyl]pyrimidine of melting point 254°–255° C.

EXAMPLE 9

In analogy to Example 7, from 2.0 g of 2,4-diamino-5-(4-piperidyl)-pyrimidine and 1.7 g of 4-fluorobenzoic acid ethyl ester there were obtained 3.1 g of ethyl p-[1-(2,4-diamino-5-pyrimidinyl)-4-piperidinyl]benzoate, m.p. above 250° C. (from dimethyl sulfoxide).

EXAMPLE 10

2.1 g of the benzoate obtained in Example 9 was dissolved in a mixture of 15 ml of conc. hydrochloric acid and 20 ml of water and stirred at 60° C. overnight. The resulting suspension was cooled to room temperature, adjusted to pH 8 by addition of ammonia and filtered. Washing the residue with water and drying gave p-[1-(2,4-diamino-5-pyrimidinyl)-4-piperidinyl]-benzoic acid of melting point 310°–311° C. (with decomposition).

EXAMPLE 11

In analogy to Example 7, from 500 mg of 2,4-diamino-5-(4-piperidinyl)-pyrimidine and 300 mg of 4-fluorobenzonitrile in 10 ml of dimethyl sulfoxide there were obtained 250 mg of 2,4-diamino-5-[1-(p-cyanophenyl)-4-piperidinyl]pyrimidine, m.p. >250° C. (from dimethyl sulfoxide).

EXAMPLE 12

In analogy to Example 1, from 4.1 g of exo-4-chloro-2,6-diamino-5-[8-(2,5-dimethoxyphenyl)-8-azabicyclo[3.2.1]oct-3-yl]pyrimidine there were obtained 2.4 g of exo-2,4-diamino-5-[8-(2,5-dimethoxyphenyl)-8-azabicyclo[3.2.1]oct-3-yl]-pyrimidine, m.p. 270° C. (from methanol).

The starting material was prepared in analogy to the process described in Example 1, paragraph A-D, starting from 8-(2,5 dimethoxyphenyl)-8-azabicyclo[3.2.1]octan-3-one, m.p. 66°–67° C. (from ether), via ethyl cyano-[8-(2,5 dimethoxyphenyl)-8-azabicyclo[3.2.1]oct-anylidene]acetate (yellowish oil), ethyl rac-(exo)-α-cyano-[8-(2,5 dimethoxyphenyl)-8-azabicyclo[3.2.1]octane-3]acetate (oil) and exo-2,6-diamino-5-[8](2,5 dimethoxyphenyl)-8-azabicyclo[3.2.1]oct-3-yl]-4-[3H]-pyrimidinone, m.p. 164° C. (from methanol-water).

EXAMPLE 13

In analogy to Example 1, from 0.18 g of exo-4-chloro-2,6-diamino-5[8-(1-naphthyl)-8-azabicyclo[3.2.1]oct-3-yl]pyrimidine there were obtained 55 mg of exo-2,4-diamino-5-[8-(1-naphthyl)-8-azabicyclo[3.2.1]oct-3-yl]pyrimidine, m.p. 245°–248° C. (from methanol).

The starting material was prepared in analogy to the process described in Example 1, paragraph A-D, starting from 8-(1-naphthyl)-8-azabicyclo[3.2.1]octan-3-one, m.p. 114°–115° C., via ethyl cyano-[8-(1-naphthyl)-8-azabicyclo[3.2.1]octanylidene]-acetate, m.p. 111°–114° C., ethyl rac-(exo)-α-cyano-[8-(1-naphthyl)-8-azabicyclo[3.2.1]octane-3]acetate (yellowish oil) and exo-2,6-diamino-5-[8-(1-naphthyl)-8-azabicyclo[3.2.1]oct-3-yl]-4-[3H]pyrimidinone, m.p. 275° C. (dec.) (from methanol-water).

EXAMPLE 14

In analogy to Example 1, from 0.3 g of exo-4-chloro-2,6-diamino-5-[8-(2-naphthyl)-8-azabicyclo[3.2.1]oct-3-yl]pyrimidine there were obtained 200 mg of exo-2,4-diamino-5-[8-(2-naphthyl)-8-azabicyclo[3.2.1]oct-3-yl]pyrimidine, m.p. 258°–9° C. (from methanol).

The starting material was prepared in analogy to the process described in Example 1, paragraphs A-D, starting from 8-(2-naphthyl)-8-azabicyclo[3.2.1]octan-3-one, m.p. 120°–1° C., via ethyl cyano-[8-(2-naphthyl)-8-azabicyclo[3.2.1]octanylidene]-acetate, m.p. 122°–3° C., ethyl rac-(exo)-α-cyano-[8-(2-naphthyl)-8-azabicyclo[3.2.1]-octane-3]acetate, m.p. 126°–7° C., and exo-2,6-diamino-5-[8-(2-naphthyl)-8-azabicyclo[3.2.1]oct-3-yl]-4-[3H]pyrimidinone, m.p. 275° C. (dec.) (from methanol-water).

We claim:

1. A method for treating malaria which comprises administering to a host in need of said treatment an effective amount for treating malaria of a compound of the formula I or a salt thereof

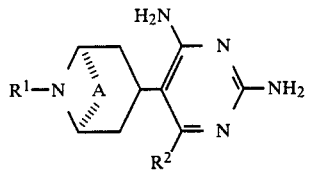

wherein $R^1$ is naphthyl, or naphthyl or phenyl singly substituted by lower-alkyl, lower alkylthio, lower alkoxy, halogen, amino, lower-alkylamino, di(lower-alkyl)-amino, nitro, trifluoromethyl, lower-alkoxycarbonyl, carboxyl, cyano or —CONHR$^3$ wherein R$^3$ is hydrogen, lower-alkyl or the residue which is formed by removal of an amino group from an amino acid $R^3NH_2$; or phenyl di- or tri-substituted by lower-alkoxy; $R^2$ is hydrogen or lower-alkoxy; and A is an optionally present ethylene or 1,3-propylene, and wherein the diaminopyrimidine group has the exo-configuration wherein A is present.

2. A method in accordance with claim 1, wherein $R^1$ is phenyl singly, di- or tri-substituted by lower alkoxy.

3. A method in accordance with claim 2, wherein $R^1$ is 4-methoxyphenyl; 3,5-dimethoxyphenyl or 3,4,5-trimethoxyphenyl.

4. A method in accordance with claim 3, wherein the compound of formula I is exo-2,4-diamino-5-[8-(3,5-dimethoxyphenyl)-8-azabicyclo[3.2.1]oct-3-yl]pyrimidine.

5. A method in accordance with claim 3, wherein the compound of formula I is 2,4-diamino-5-[1-(3,5-dimethoxyphenyl)-4-piperidinyl]pyrimidine.

* * * * *